(12) United States Patent
Qadeer

(10) Patent No.: US 9,072,517 B2
(45) Date of Patent: Jul. 7, 2015

(54) NATURAL ORIFICE TRANSLUMINAL ENDOSCOPIC DEVICES FOR CLOSURE OF LUMINAL PERFORATIONS AND ASSOCIATED METHODS

(75) Inventor: Mohammed Abdul Qadeer, Lewisville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 732 days.

(21) Appl. No.: 13/295,417

(22) Filed: Nov. 14, 2011

(65) Prior Publication Data

US 2012/0209318 A1    Aug. 16, 2012

Related U.S. Application Data

(60) Provisional application No. 61/413,605, filed on Nov. 15, 2010.

(51) Int. Cl.
| | |
|---|---|
| A61B 17/08 | (2006.01) |
| A61B 17/10 | (2006.01) |
| A61B 17/068 | (2006.01) |
| A61B 17/04 | (2006.01) |
| A61B 17/00 | (2006.01) |
| A61B 17/064 | (2006.01) |

(52) U.S. Cl.
CPC ............ *A61B 17/10* (2013.01); *A61B 17/0401* (2013.01); *A61B 17/0682* (2013.01); *A61B 17/08* (2013.01); *A61B 2017/00004* (2013.01); *A61B 2017/00269* (2013.01); *A61B 2017/00278* (2013.01); *A61B 2017/00477* (2013.01); *A61B 2017/00862* (2013.01); *A61B 2017/00867* (2013.01); *A61B 2017/0641* (2013.01); *A61B 2017/0645* (2013.01)

(58) Field of Classification Search
CPC .......... A61B 17/0401; A61B 17/0682; A61B 17/08; A61B 17/083; A61B 17/10; A61B 17/1285; A61B 2017/0641; A61B 2017/0645
USPC ........................................ 606/213, 216, 221
See application file for complete search history.

(56) References Cited

U.S. PATENT DOCUMENTS

| | | | | |
|---|---|---|---|---|
| 5,893,856 A * | 4/1999 | Jacob et al. | .................. | 606/151 |
| 6,142,957 A | 11/2000 | Diamond et al. | | |
| 6,155,968 A * | 12/2000 | Wilk | .............................. | 600/16 |
| 8,048,108 B2 * | 11/2011 | Sibbitt et al. | .................. | 606/213 |

(Continued)

OTHER PUBLICATIONS

Anson, Tony, *Shape Memory Alloys-Medical Applications*, printed from the internet on Nov. 11, 2010, http://www.axom.com/details.asp?ArticleID=134, Source: Materials World, Dec. 1999, pp. 745-747, vol. 7, No. 12.

(Continued)

*Primary Examiner* — Gregory Anderson
(74) *Attorney, Agent, or Firm* — Myers Bigel Sibley & Sajovec, P.A.

(57) ABSTRACT

Devices include at least two spaced apart flexible legs formed of a shape memory material, each leg having a respective free end configured to engage local tissue. The devices can also include at least one resilient member having opposing end portions, a respective end portion being attached to each leg at a location away from the free end. The resilient member is configured to take on a stretched configuration inside an endoscope during delivery. Alternatively or additionally, the devices include a cinch that is configured to snugly hold portions of both legs to force the legs closer together.

13 Claims, 18 Drawing Sheets

(56) References Cited

U.S. PATENT DOCUMENTS

| | | | |
|---|---|---|---|
| 8,500,760 B2* | 8/2013 | McLawhorn | 606/151 |
| 2002/0045909 A1* | 4/2002 | Kimura et al. | 606/151 |
| 2005/0182426 A1* | 8/2005 | Adams et al. | 606/142 |
| 2006/0058817 A1* | 3/2006 | Starksen et al. | 606/142 |
| 2008/0221599 A1* | 9/2008 | Starksen | 606/157 |
| 2011/0093009 A1* | 4/2011 | Fox | 606/216 |
| 2012/0226287 A1 | 9/2012 | Qadeer | |

OTHER PUBLICATIONS

Kirschniak et al., *A new endoscopic over-the-scope clip system for treatment of lesions and bleeding in the GI tract: first clinical experiences*, Gastrointestinal Endoscopy, 2007, pp. 162-167, vol. 66, No. 1.

Lendlein et al., *Light-induced shape-memory polymers*, Nature, Apr. 14, 2005, pp. 879-882, vol. 434.

Lendlein et al., *Biodegradable, Elastic Shape-Memory Polymers for Potential Biomedical Applications*, Science, May 31, 2002, pp. 1673-1676, vol. 296.

Lendlein et al., *Shape-Memory Polymers*, Angew. Chem. Int. Ed., 2002, pp. 2034-2057, vol. 41.

Leng et al., Comment on "*Water-driven programmable polyurethane shape memory polymer: Demonstration and mechanism*," Applied Physics Letters, 2008, pp. 206105-1 and 206105-2, vol. 92.

Mohr et al., *Initiation of shape-memory effect by inductive heating of magnetic nanoparticles in thermoplastic polymers*, PNAS, Mar. 7, 2006, pp. 3540-3545, vol. 103, No. 10.

Perretta et al., *A new method to close the gastrotomy by using a cardiac septal occlude: long-term survival study in a procine model*, Gastrointestinal Endoscopy, 2007, pp. 809-813, vol. 66, No. 4.

Teoh et al., *Current developments in natural orifices transluminal endoscopic surgery: An evidence-based review*, World Journal of Gastroenterology, Oct. 14, 2010, pp. 4792-4799, vol. 16, Issue 38.

* cited by examiner

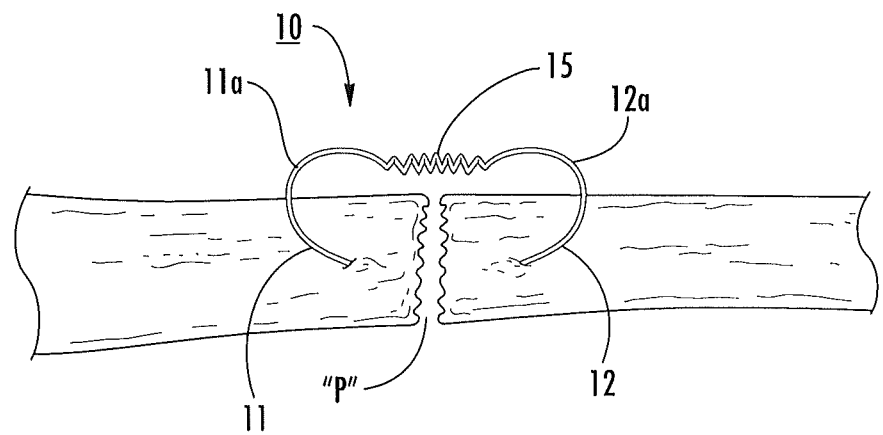
FIG. 1
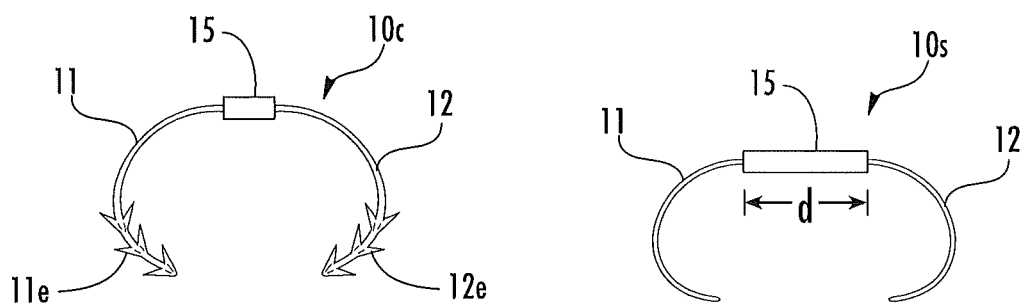
FIG. 2A
FIG. 2B
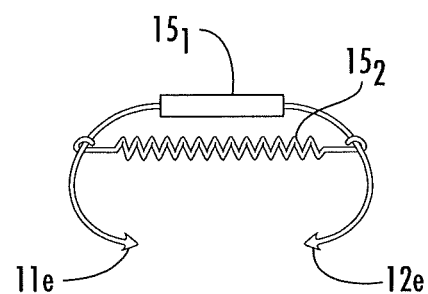
FIG. 2C

NATURAL ORIFICE TRANSLUMINAL ENDOSCOPIC DEVICES FOR CLOSURE OF LUMINAL PERFORATIONS AND ASSOCIATED METHODS

RELATED APPLICATIONS

This application claims the benefit of and priority to U.S. Provisional Application No. 61/413,605, filed Nov. 15, 2010, the contents of which are hereby incorporated by reference as if recited in full herein.

FIELD OF THE INVENTION

This invention relates to surgical devices that may be particularly useful for closing luminal perforations in endoscopic procedures.

BACKGROUND OF THE INVENTION

Natural orifices transluminal endoscopic surgery (NOTES) is a promising technology, but obstacles remain that inhibit the commercial use of the procedures in human patients including, for example, safe closure at a point of access.

SUMMARY OF EMBODIMENTS OF THE INVENTION

Embodiments of the invention are directed to devices and methods for NOTES procedures.

Some embodiments are directed to medical devices. The devices include at least two spaced apart flexible legs formed of a shape memory material, each leg having a respective free end configured to engage local tissue.

The devices can also include at least one resilient member having opposing end portions, a respective end portion being attached to each leg at a location away from the free end. The resilient member is configured to take on a stretched configuration inside an endoscope during delivery. Alternatively or additionally, the devices include a cinch that is configured to snugly hold portions of both legs to force the legs closer together.

The device can include the at least one resilient member. The at least one resilient member can be two, one attached to end portions of a first two of the legs and the other attached to a second two of the legs. Implanted, the legs can have a curvilinear shape and end portions away from the respective free ends can be joined by the resilient member.

The device can include the cinch. The legs can be defined by a continuous length of a shape memory material that is pre-shaped to have the two legs and an intermediate crown. Each leg can have a pre-formed curvilinear shape. The crown can have a cinch retention shape that resides outside the cinch body on a side opposing the free ends of the legs.

Yet other embodiments are directed to endoscopic device delivery tools. The tools include a device sized and configured to be held in an endoscope lumen. The device has at least two flexible elongate legs formed of a shape memory material and having free end portions configured to attach to target tissue. The legs are configured to have a substantially straight configuration in the endoscope lumen and a pre-formed curvilinear shape after deployment.

The delivery tool may also include a sheath configured to enclose the closure device and reside inside the endoscope lumen and at least one elongate structure attached to the closure device to be able to slidably deploy the device from the endoscope. Optionally, a distal end portion of the sheath is configured to slidably exit the endoscope lumen while holding at least a portion of the closure device therein.

The device may include a resilient member. The at least one elongate structure can be a tripod attachment structure that releasably holds the closure device at three locations so that the resilient member is held in a "V" shape inside the sheath. The tool can be configured to substantially concurrently release the tripod attachment structure after the legs of the closure device engage target tissue so that upon deployment from the sheath, the resilient member automatically pulls the legs closer together.

The device can include a cinch that is configured to snugly hold a length of the legs of the device close together. The cinch can be slidably deployable out of the sheath using the at least one attachment structure.

The device can include a continuous length of a shape memory material that is pre-shaped to have the two legs and an intermediate crown. The at least one attachment structure can include a first structure releasably attached to the cinch and a second structure releasably attached to the crown to slidably advance the shape memory material legs out of the sheath before the cinch is released from the sheath.

The free end portions of the legs outside the endoscope can face the endoscope and reside against or in tissue in a side of a hollow visceral wall opposing a side that the endoscope is located on. Alternatively, the free end portions of the legs outside the endoscope face away from the endoscope.

Still other embodiments are directed to natural orifice transluminal endoscope surgical methods. The methods include: (a) providing an endoscope with a closure device comprising at least two flexible legs having a respective free end, each leg formed of shape memory material held in a substantially linear shape in the endoscope; (b) inserting the endoscope in a natural orifice of a patient to carry out a natural orifice transluminal surgery; then (c) deploying the legs from the endoscope whereby the legs return to a curvilinear configuration; (d) attaching the legs to target tissue; and (e) pulling the legs closer together to pull the respective target tissue closer together.

The deploying step can be carried out so that the free end portions of the legs face the endoscope and reside against or in tissue in a side of a hollow visceral wall opposing a side that the endoscope is located on.

The deploying step can be carried out so that the free end portions of the legs face away from the endoscope to close a mucosal defect or to treat GI bleeding.

The device can have at least one resilient member. The method can also include, before the deploying step, holding the resilient member in a stretched configuration. The pulling step can be carried out by releasing the resilient member from the stretched configuration.

The device can include a cinch. The pulling step can be carried out by sliding the cinch toward the free ends of the legs or by sliding the legs inside the cinch away from the target tissue to force the legs closer together.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 1 is a schematic illustration of a closure device in position for approximation of a perforation associated with a NOTES procedure according to embodiments of the present invention.

FIGS. 2A and 2B are schematic illustrations of a closure device that has a resilient member that can change lengths between stretched and non-stretched configurations according to embodiments of the present invention.

FIG. 2C is a schematic illustration of a closure device with two resilient members according to embodiments of the present invention.

DESCRIPTION OF EMBODIMENTS OF THE INVENTION

Figure 3:
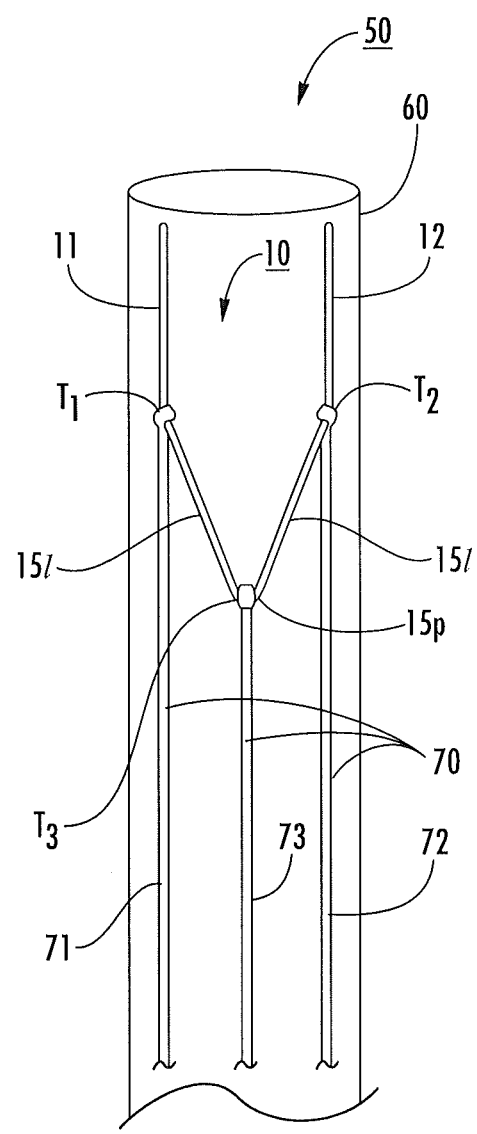
FIG. 3 is a partial schematic illustration of a surgical delivery tool configured to deliver a closure device using an endoscope according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

Embodiments of the invention are useful for veterinarian and human uses as well as for animal studies. That is, methods and devices provided by embodiments of the invention can be configured for any species of interest, e.g., mammalian including human, simian, mouse, rat, lagomorph, bovine, ovine, caprine, porcine, equine, feline, canine, and the like.

Embodiments of the invention may be particularly suitable for closing luminal perforations associated with a NOTES procedure. The term "perforation" and derivatives thereof refer to an aperture formed in tissue or a defect in tissue, such as mucosal defects created during endoscopic polypectomy or apertures intentionally formed for endoscopic removal of a gall bladder (for example) via a hole created in the stomach.

It is noted that there are two primary differences between laparoscopic surgeries and NOTES. The first one is access, laparoscopic access is through the abdominal wall, while NOTES access is through the natural orifices such as mouth, nasal, rectum, urethra, vagina and the like. The second difference is that laparoscopic surgery uses rigid instruments while NOTES uses flexible instruments.

Generally stated, most NOTES procedures include: (a) passing one or more flexible instruments through a natural orifice; (b) creating a perforation (e.g., in a visceral hollow organ); (c) passing the instrument out of the perforation (e.g., hollow viscera into an abdominal cavity) to perform a desired surgery; and (d) closing the perforation. In some embodiments, the devices may be particularly useful for carrying out NOTES to remove a gall bladder via the stomach. However, it is contemplated that according to some embodiments, an endoscopic polypectomy or endoscopic closure of mucosal defects can be performed. Thus, embodiments of the invention can provide useful tools to approximate large defects and may decrease the frequency of colon resections, particularly those resections used for large polyps. In yet other embodiments, the devices can be used to treat gastrointestinal bleeding. Thus, the term "closure device" refers to a device that is used to pull spaced apart tissue closer together or treat local tissue.

The term "resilient" refers to the ability of the so-called component to substantially return to its original length after being stretched. The term "band" is used broadly and refers to a length of a flexible biocompatible material (which is sterile for medical use). The band can be formed of any suitable material or combination of materials and may be configured for chronic implantation at the point of access closure site. The term "shape memory material" refers to materials that are able to take on a defined pre-formed (expanded) shape after being deformed into a different (collapsed, temporary) shape prior to release from a delivery device. Examples of such materials includes Ni—Ti alloys (such as Nitinol). Other shape memory alloys that may be suitable for medical use include one or more of the following alloys.

| | |
|---|---|
| Titanium-palladium-nickel | Iron-manganese-silicon |
| Nickel-titanium-copper | Nickel-titanium |
| Gold-cadmium | Nickel-iron-zinc-aluminium |
| Iron-zinc-copper-aluminium | Copper-aluminium-iron |
| Titanium-niobium-aluminium | Titanium-niobium |
| Uranium-niobium | Zirconium-copper-zinc |
| Hafnium-titanium-nickel | Nickel-zirconium-titanium |

The term "shape memory materials" also includes shape memory polymers (SMPs) and can include biodegradable SMPs. SMPs are polymeric smart materials that have the ability to return from a deformed state (temporary shape) to their original (permanent) shape induced by an external stimulus, such as temperature change. See, e.g., Lendlein, A., Kelch, S., (2002), "Shape-memory polymers," *Angew, Chem. Int. Ed.* 41: 2034-2057; and Lendlein, A., Langer, R., (2002), "Biodegradable, Elastic Shape Memory Polymers for Potential Biomedical Applications," *Science* 296 (5573). Most SMPs can retain two shapes (others can retain three) and the transition between those is induced by the external stimulus, such as temperature. In addition to a temperature-based stimulus, the shape change of SMPs can be triggered by an electric or magnetic field, light exposure (e.g., UV light) or a (gas/liquid) fluid. See, e.g., Mohr, R. et al. (2006), Initiation of shape-memory effect by inductive heating of magnetic nanoparticles in thermoplastic polymers," *Proc. Natl. Acad. Sci. USA.* 103 (10): 3540-3545; Lendlein, A. et al., (2005), "Light-induced shape-memory polymers," *Nature* 434 (7035): 879-882; and Jinsong Leng, Haibao Lv, Yanju Liu and Shanyi Du., (2008), "Comment on "Water-driven programmable polyurethane shape memory polymer: Demonstration and mechanism," *Appl. Phys. Lett.* 92: 206105. The contents of the above articles are hereby incorporated by reference as if recited in full herein.

Turning now to the figures, FIG. 1 illustrates an exemplary NOTES closure device 10 at the target closure site "P" associated with approximation of a perforation created during a NOTES procedure. The device 10 is a flexible clip or clamp-like device that has two legs 11, 12 separated by a resilient member 15. The resilient member 15 can be described as a crown with opposing end portions, each end portion attached to one end of a respective leg 11, 12. The other ends of the legs 11, 12 are free so as to be able to contact local tissue as shown in FIG. 1. The legs 11, 12 are formed from a shape memory material so that they can be collapsed inside an endoscope for intraluminal delivery to a closure site as will be discussed further below. The resilient member 15 can comprise a flexible elastomeric (e.g., polymeric or rubber) band, a woven or braided resilient stretchable material, a (coil) spring, a length of elastic SMP, or other resilient member, or combinations of different types of resilient members. The legs 11, 12 and the resilient member 15 can be relatively thin. The legs 11, 12 can have a diameter or cross-sectional width/height of between about 1 mm to about 5 mm with typical lengths being between about 10-30 mm. In some embodiments, the closure device 10 can be used for perforation diameters of between about 10 mm to about 25 mm.

The resilient member can have a width/height, typically diameter, that is between about 1 mm to about 5 mm and have sufficient resiliency or elasticity to be able to pull the legs of the device 11, 12 together to close the target opening, perforation or defect P. In some embodiments, the resilient member 15 has a length that is between about 20% to about 50% the length of a respective leg or prong 11, 12.

As shown in FIG. 2B, the closure device 10 can have a stretched configuration 10s where the resilient member 15 is stretched a distance "d" as shown in FIG. 2B and a closed (shorter length) configuration 10c as shown in FIG. 2A where the resilient member 15 is collapsed to pull the legs 11, 12 closer together. The maximum distance "d" is typically between about 0.1 mm to about 25 mm, and more typically between about 1 mm to about 25 mm. For example, the resilient member 15 can have a non-stretched length of between about 1 mm to about 5 mm, typically between about 2 mm to about 4 mm, and a stretchable length of between about 5 mm to about 20 mm. The resilient member 15 is typically configured to be able to stretch at least about 20% relative to its deployed, implanted length. The maximum stretch "d" is typically introduced when the device 10 is held in the endoscope during placement in the body, prior to deployment. The closed or non-stretched configuration 10c can automatically occur as the device 10 is released from the endoscope. The legs 11, 12 will have more structural rigidity than the crown 15, which will have more resiliency so that it can change in length and provide the desired resiliency to bring the legs together to close the aperture/defect. Thus, the legs 11, 12 can be formed of a different material than the resilient member 15 (e.g., crown).

The free ends of the legs (that engage local tissue) may be barbed, pointed or comprise an anti-slip coating or sleeve 11e, 12e (FIG. 2C) to facilitate tissue grasping. The device 10 can be configured as a traumatic type or atraumatic type device. Each end or even each leg of the device may have a different configuration. The legs 11, 12 can comprise a medicament and/or pharmaceutical coating to promote healing, such as a coating comprising an anti-inflammatory and/or an antibiotic or the like.

As shown in FIGS. 1, 2A and 2B, the device 10 can be configured so that the legs 11, 12 are curvilinear. As shown, the legs 11, 12 typically have substantially arcuate or semi-circular portion when deployed from the endoscope. In some embodiments, the legs 11, 12, when in position engaged with or in target tissue, have an uppermost portion 11a, 12a (as shown) or lowermost or outermost portion, depending on orientation in the body, being laterally spaced apart from and above or at about the height of the resilient member 15. However, other pre-formed shapes can be used as long as the legs are sufficiently structurally strong to be able to engage local tissue and pull the spaced apart regions of target tissue closer (typically totally) together.

FIG. 2C illustrates that the device 10 can include two resilient members $15_1$, $15_2$, that may provide additional tensile closure force on the legs 10, 11. The resilient members can comprise different elastic materials or configurations, e.g., thicker and longer bands or one spring and one band and the like. It is also noted that additional resilient members may also be used. Alternatively, the device 10 can include a single resilient member 15 which resides inwardly from the upper end of the device 10 similar to the position of member $15_2$.

In some embodiments, the closure device 10 can remain implanted in the body as a chronic implanted device similar to conventional medical clips. In other embodiments, the device 10 can be extracted after a suitable time. For example, in some particular embodiments, a suture or retrieval string can remain attached to the closure device for ease of retrieval into an endoscope, catheter or other enclosure after a suitable time.

In particular embodiments, the legs 11 and resilient member 15 can be formed of biodegradable materials. For example, both the legs 11, 12 can comprise a biodegradeable SMP and the crown 15 can comprise a biodegradeable elastic material.

FIG. 3 illustrates an exemplary delivery tool 50 for placing the closure device 10 using an endoscope 100. As shown, the tool 50 includes a hollow elongate (e.g., cylindrical) polymeric outer sheath 60 that encloses the closure device 10 and deforms the legs 11, 12 to have a substantially straight shape. The sheath 60 can have a size that is about 10 French. However, other sizes may also be used. The length of the tool 50 can be between about 230 cm to about 240 cm, but other lengths may also be used. The closure device 10 is typically held in the sheath 60 with the free ends of the legs facing outward. The resilient member 15 is held in a state of stretch with the member 15 held in a "V" like shape with the peak 15p held medially (side to side) in the sheath, in a direction away from the legs 11, 12. The member 15 is oriented with lengths thereof tapering outward toward the sheath wall in the direction of the legs 11, 12. As shown, the device 10 is held in the sheath 60 using a tripod attachment arrangement 70 with releasable anchor points T1, T2, and T3 and corresponding slidably advanceable tripod members 71, 72, 73 extending in the sheath 60. The tripod attachment 70 is configured to releasably attach to the closure device 10, stretch or expand the resilient member 15, and may protide support to the legs 11, 12.

Figure 4:
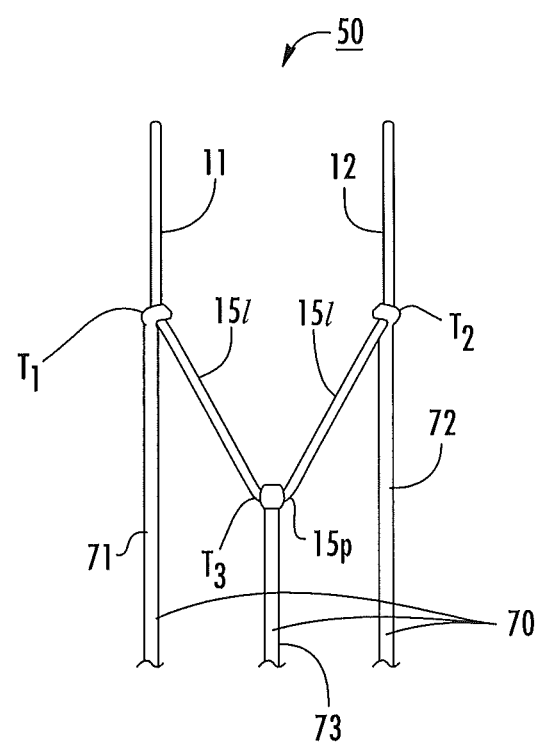
FIG. 4 is an enlarged partial view of the delivery tool shown in FIG. 3 but illustrated without an outer sheath according to embodiments of the present invention.
Figure 5:
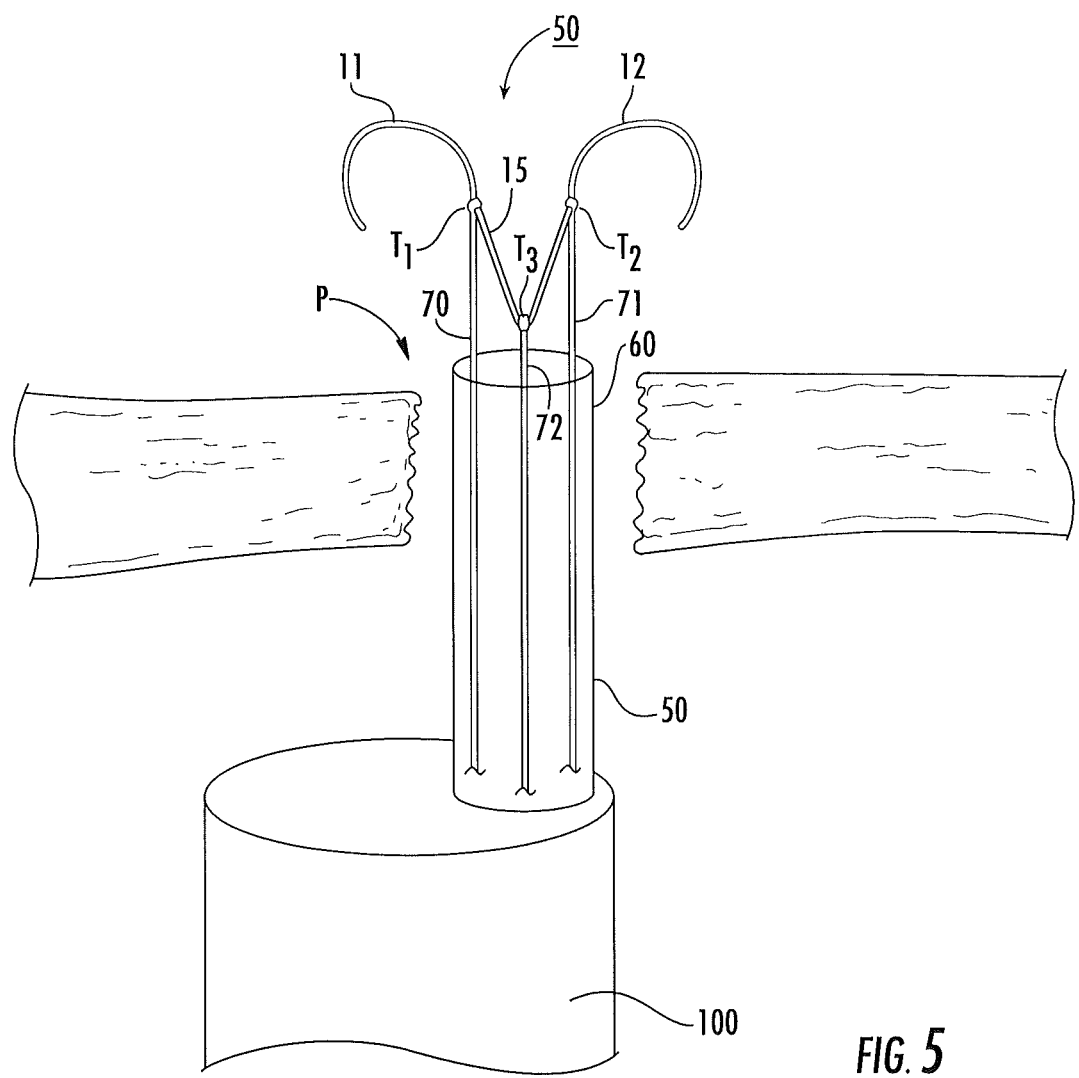
FIGS. 5-7 are schematic illustrations of a sequence of actions that can be carried out to deploy the closure device using the tool shown in FIG. 3 according to embodiments of the present invention.
Figure 6:
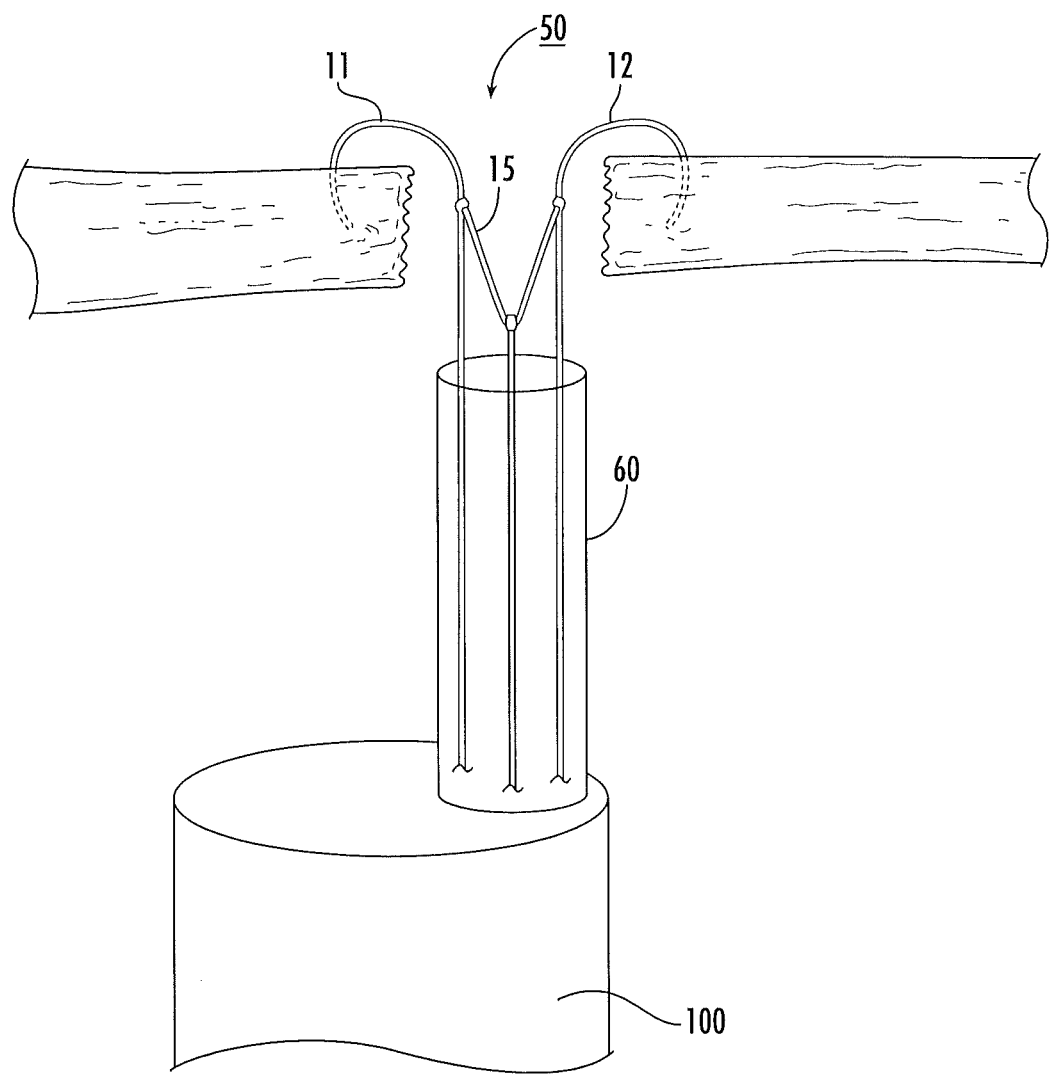
Figure 7:
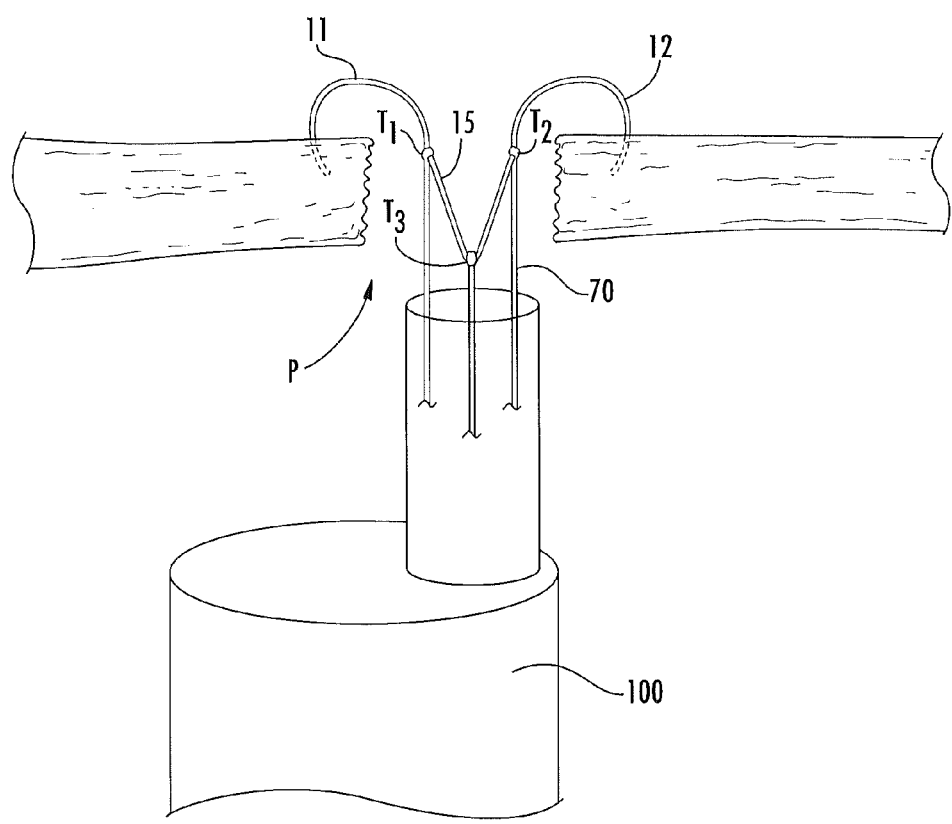

The tripod members 71, 72, 73 can be wires, sutures, sleeves, tubes or other elongate components that can be selectively slid forward to push the closure device 10 out of the sheath 60 for deployment at the closure site (FIGS. 5-7). FIG. 4 is an enlarged view of the closure device 10 and tripod attachment 70 shown in FIG. 3 with the sheath 60 omitted.

The end portions of the tripod members 71, 72, 73 can have loops, hooks or other configurations that can attach to the desired anchor points on the closure device 10 and rotate or otherwise translate or be severed to release the legs 11, 12 and resilient member 15 during deployment.

Figure 8A:
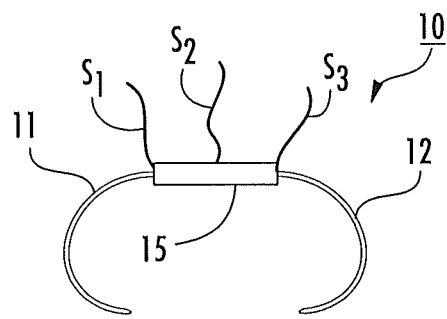
FIG. 8A is a schematic illustration of a closure device that may have attached lengths of sutures according to embodiments of the present invention.

In some particular embodiments, the attachment anchor points T1, T2, T3 can be configured using attached lengths of sutures (e.g., tied, swaged, via heat-shrink and/or adhesively attached lengths of sutures). These attachment lengths of suture segments can be in communication with wires, larger sutures, sleeves or other structures that provide sufficient rigidity and/or tension to hold the anchor points and the stretched configuration of the member 15. The suture attachments can be cut proximate to or upstream of the anchor points T1, T2, T3 at the desired deployment time to release the closure device in situ. Small lengths of the attachment sutures S1, S2, S3 can be deployed with the closure device 10 (FIG. 8A). The sutures segments S1, S2, S3 can be biodegradeable.

FIGS. 5-7 illustrate a series or sequence of steps that can be carried out using the delivery tool 50 to place the closure device 10 in situ. As shown in FIG. 5, the delivery tool (e.g., sheath 60) is slidably advanced a distance beyond the distal end of the endoscope 100, typically through the perforation P in the hollow visceral wall. The tripod arrangement 70 (typically each of the structures 71, 72, 73 are slid forward concurrently) slidably advances at least the forward portions of the legs 11, 12 of the closure device 10 outside the sheath 60. The legs 11, 12 take on the pre-formed shape. As shown in FIG. 6, the legs 11, 12 are pulled rearward to anchor in or against the hollow visceral wall. Typically, the tripod attachment 70 is still attached to the legs 11, 12 and the resilient member 50. As shown in FIG. 7, the attachment/anchor points T1, T2, T3 can be released substantially concurrently, allowing the resilient member 15 to return to a smaller length and pulling the legs engaged in the tissue together to close the perforation P (FIG. 1). The closure device 10 can reside on one side of the closed perforation P and the endoscope can reside on the other.

While the delivery tool is shown as using the sheath 60, in some embodiments, it is contemplated that an endoscope lumen wall can enclose the tripod structure 70 and closure device 10 and the sheath is not required. Further, while it is contemplated that concurrent release of all three attachment points T1, T2, T3 is typical. In other embodiments, the attachments T1, T2 to the respective leg 11, 12 can be released before the attachment T3 to the resilient member 15, the legs can be released at the same or different times, and/or the resilient member attachment T3 may be released first.

It is contemplated that other delivery systems may be used to deliver the closure devices 10', 10", 110 described herein.

Figure 8B:
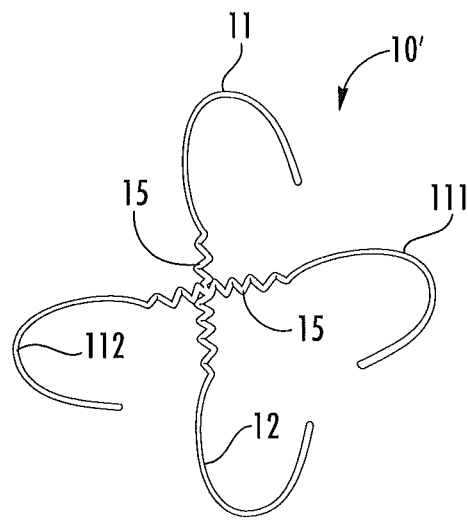
FIGS. 8B-8D are schematic illustrations of a closure device having more than two legs or prongs according to embodiments of the present invention.
Figure 8C:
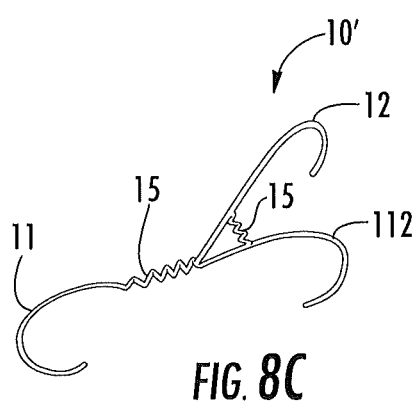
Figure 8D:
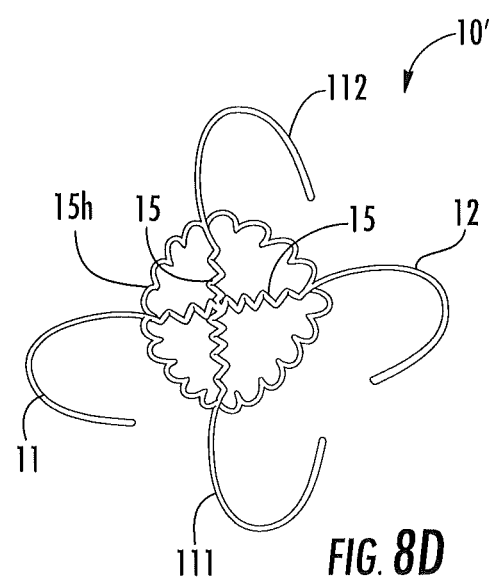

FIGS. 8B-8D illustrate that the closure device 10' can include more than two legs or prongs. FIGS. 8B and 8D show as two pair of cooperating legs 11, 12, 111, 112. FIG. 8C shows three legs 11, 12, (e.g., prongs). Although not shown, more than four legs (e.g., prongs) may also be used (not shown). Further, as shown in FIG. 8B, each pair or set of legs (e.g., prongs), shown as 11, 12 and 111, 112 can include a (bridging) resilient member 15. The two members 15 can overlap and may optionally be physically attached together. FIG. 8C illustrates that the closure device 10' includes two resilient members 15, one between leg 11 and legs 12 and 112 (e.g., the first resilient member 15 is attached to both legs 12, 112) and another spaced apart resilient member 15 between legs 12 and 112. FIG. 8D illustrates the use of a plurality of resilient members 15, one between legs 11, 12, one between legs 111, 112 and a halo resilient member 15h.

Figures 9A, 9B:
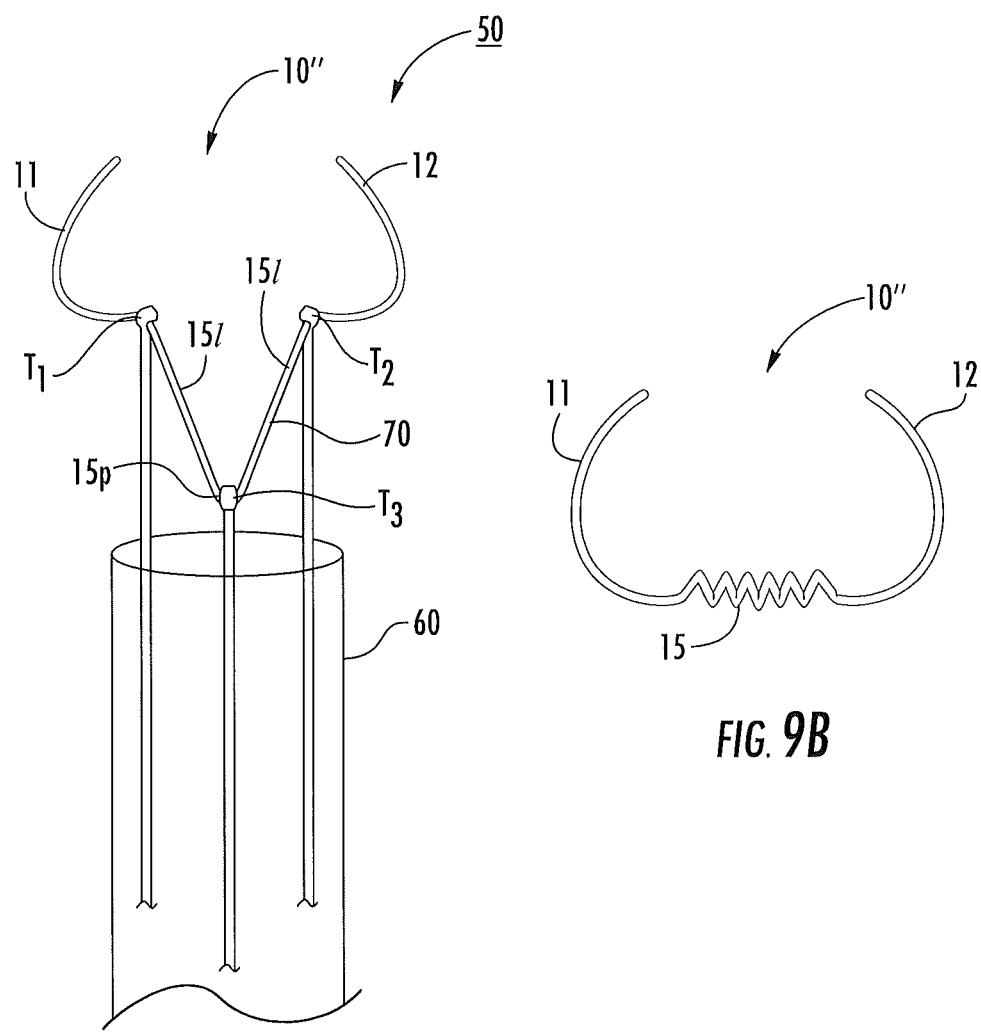
FIG. 9A is a schematic illustration of a delivery tool shown in FIG. 3 but illustrating that the closure device can have legs or prongs with a shape that opens outward rather than inward according to embodiments of the present invention.
FIG. 9B is a schematic illustration of the closure device shown in FIG. 9A after deployment from the delivery tool according to embodiments of the present invention.

FIGS. 9A and 9B illustrate an embodiment similar to that discussed above with respect to FIGS. 5-7. FIG. 9A shows the closure device 10" during deployment and FIG. 9B shows the closure device after deployment. As shown in FIG. 9A, in this embodiment the closure device 10" is configured so that the legs 11, 12 open outward rather than inward. Stated differently, the legs are configured so that the respective arcs curve toward each other rather than away from each other during deployment when unrestrained outside the sheath or endoscope (concave rather than convex). Thus, the legs or prongs open outward instead of inward, e.g., away from the endoscope rather than toward the endoscope according to embodiments of the present invention.

Figure 9C:
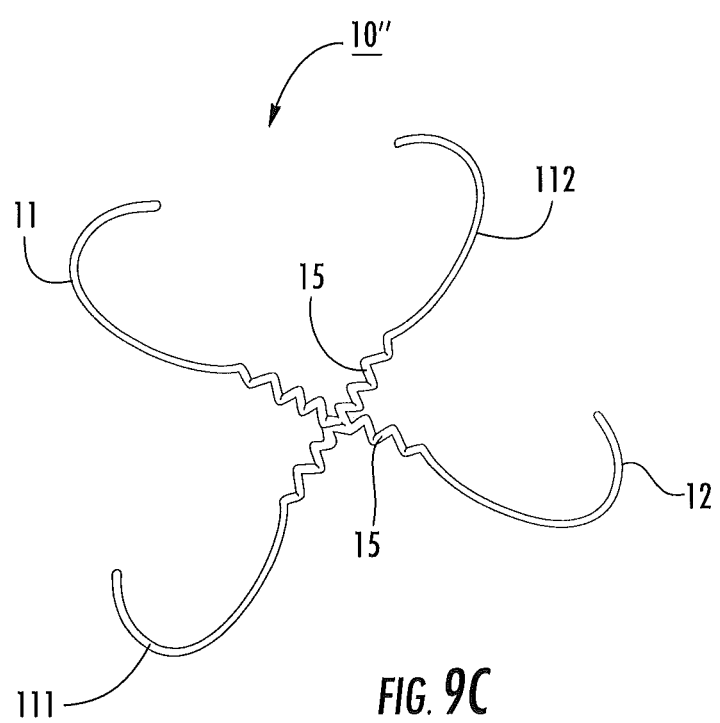
FIG. 9C is a schematic illustration of a multi-leg or pronged device similar to that shown in FIG. 8B but with the shape being outward rather than inward according to embodiments of the present invention.

This embodiment may be particularly suitable for working from within a lumen for approximating mucosal defects or control of bleeding. FIG. 9C illustrates that the closure device 10" can have more than three prongs similar to the embodiments discussed above with respect to FIGS. 8B-8O that open outward away from the sheath 60 or endoscope 100. The embodiments discussed above with respect to FIGS. 8B-8D may have legs that close either inward or outward.

Figure 10:
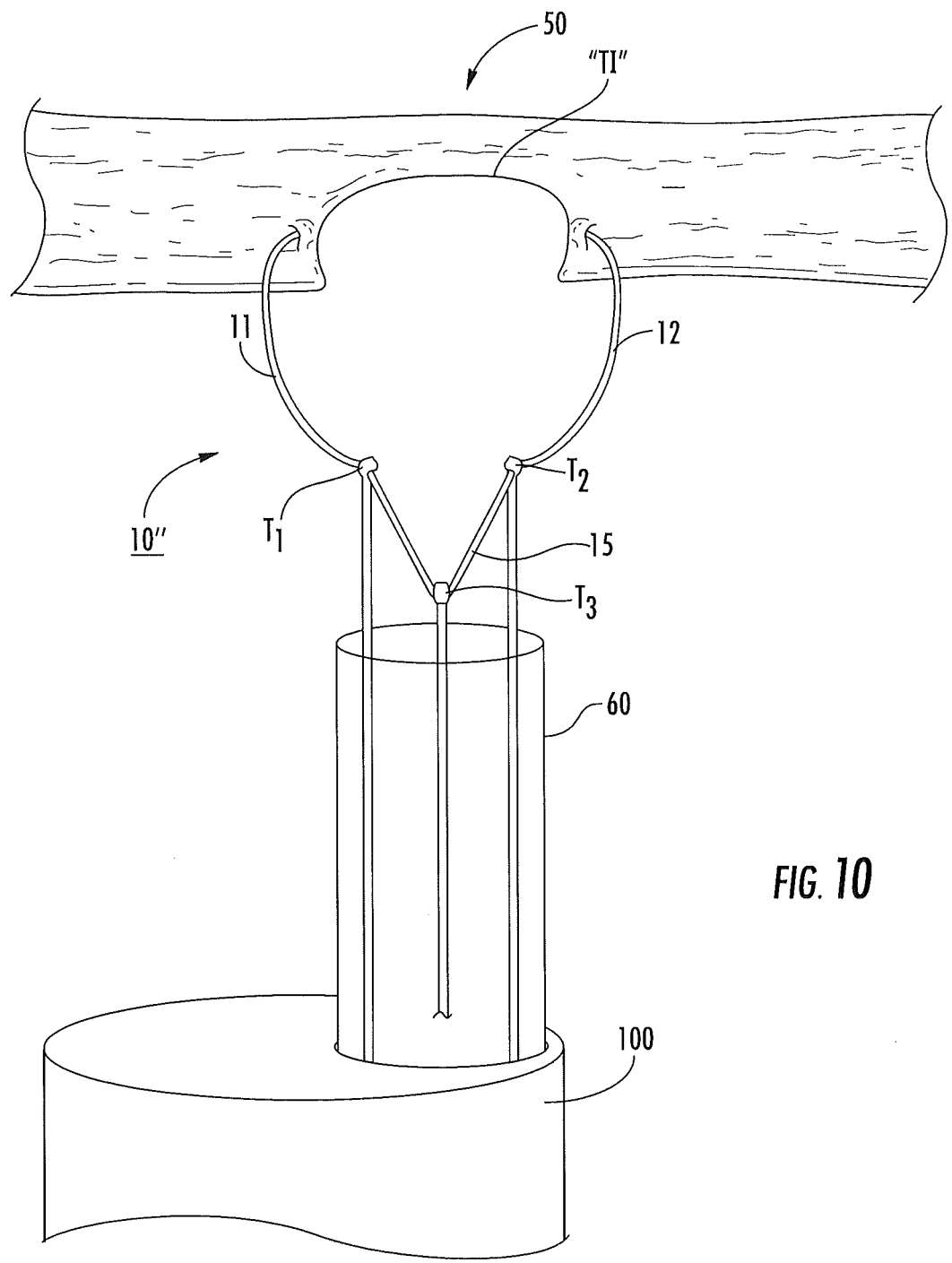
FIGS. 10 and 11 are schematic illustrations of the deployment of the closure device shown in FIGS. 9A-9C to treat GI bleeding or close a mucosal defect according to embodiments of the present invention.
Figure 11:
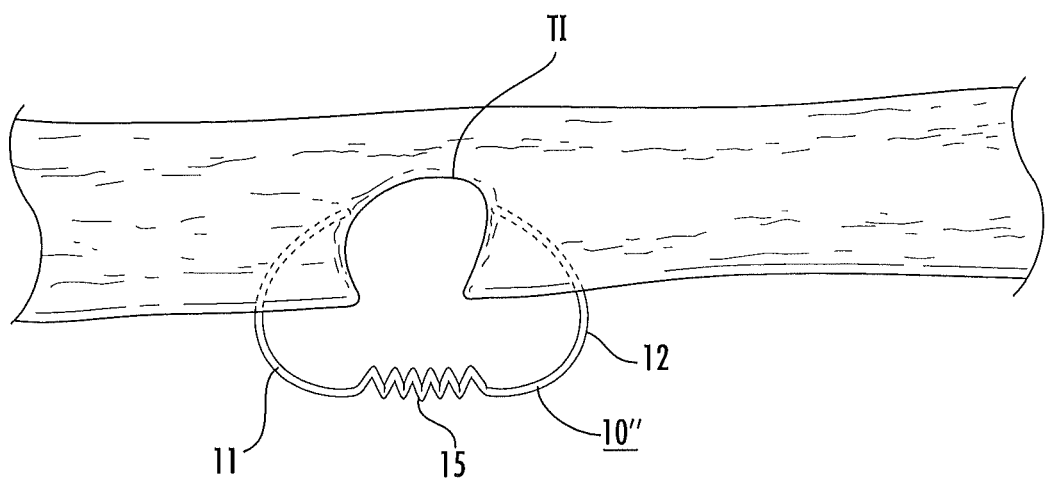

FIGS. 10-11 illustrate an exemplary deployment of the closure device 10" that can have legs that open outward to abut tissue TI to repair a mucosal defect or GI bleeding and the like (e.g., no total perforation is required). As shown in FIG. 11, the legs 11, 12 are pulled together to pull walls of a mucosal defect, pit or a tissue spot with bleeding, together on the same side of the tissue as the endoscope 100.

FIGS. 12-17 illustrate another embodiment of a delivery tool 50' and associated flexible closure device 110. As before, the tool 50' can be held in the endoscope 100 for intraluminal placement. In this embodiment, the device 110 can have a continuous length of a shape memory material (e.g., a monolithic unitary member) that defines a shape memory member 110m pre-formed to have a crown 13 and two legs 11, 12. A cinch 66 is used to pull the legs 11, 12 of the device 110 together and no stretchable resilient member 15 is required. The crown 13 may include a cinch retention shape or member 13a (e.g., an anti-dislodgement shape) (FIG. 17), such as a laterally extending knob, bulb or other projection or shape to help inhibit dislodgement of the cinch 66 to prevent the cinch from sliding rearward and off the shape memory member 110m.

In this embodiment, the cinch 66 and shape memory member 110m are held inside the delivery tool 50'. The cinch 66 can have an inner channel 66i that slidably snugly holds a length of each of the legs 11, 12. The cinch 66 can comprise a rigid or compressible body that is biocompatible and is sized and configured to reside in the endoscope during delivery to local tissue. In some embodiments, the cinch 66 can have a small tubular body. However, the cinch body 66b can have any desired shape geometric or irregular shape, such as, but not limited to, cylindrical, spherical, polygonal (long or short box-like shape), oval, teardrop and the like. The cinch 66 can have a length that is between about 2-5 mm, but other lengths may also be appropriate. In some embodiments more than one cinch 66 (attached or separate) may be used to pull the legs closer (not shown).

Figure 12:
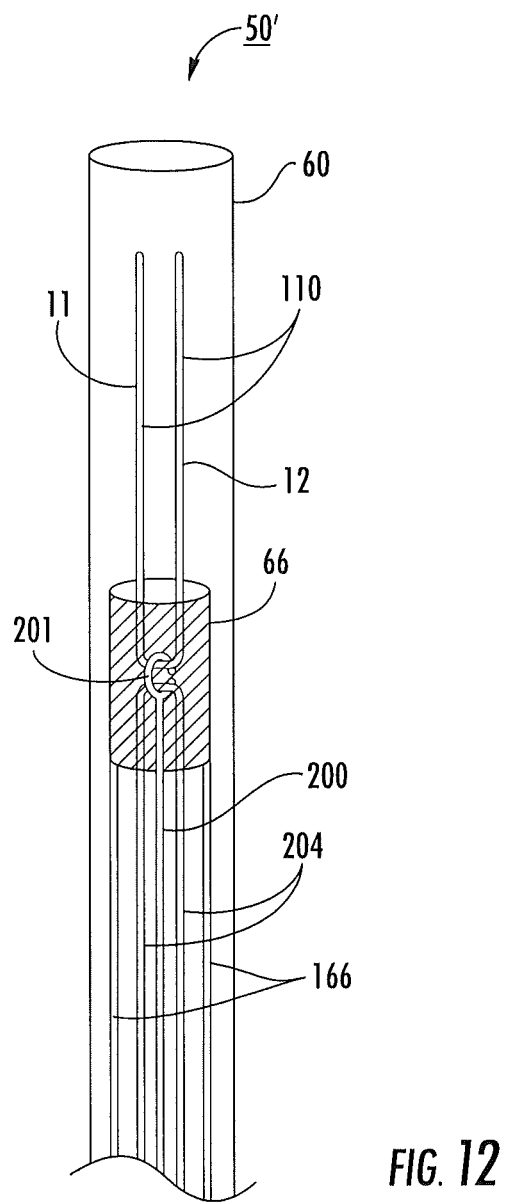
FIG. 12 is a schematic illustration of another embodiment of a closure device and associated delivery tool according to yet other aspects of the present invention.

As shown in FIG. 12, the cinch 66 is attached to at least one elongate structure 166 that slidably advances the cinch 66 in the sheath 60. Another elongate structure 200 is releasably attached to the shape memory device 110m typically via a hook 201. One or more additional elongate structures 204 can releasably attach to the shape memory structure 110m. The elongate structures can comprise wires, sutures, sleeves, tubes or other elongate components that can be selectively slid forward to push the respective component forward.

Figure 13:
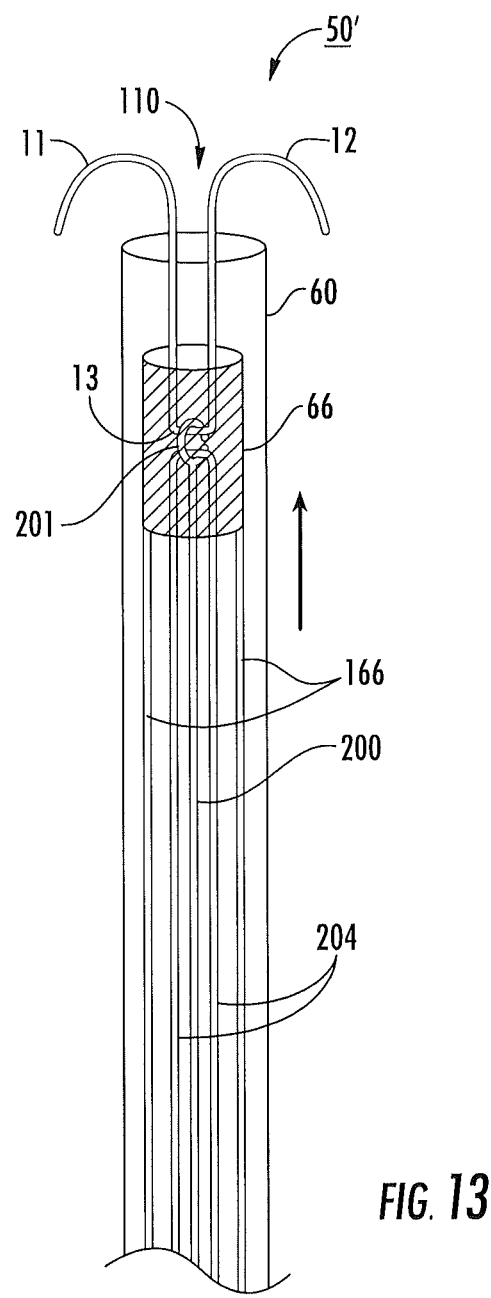
FIGS. 13-16 are schematic illustrations of a series of steps that can be used to deploy the closure device shown in FIG. 12.
Figure 14:
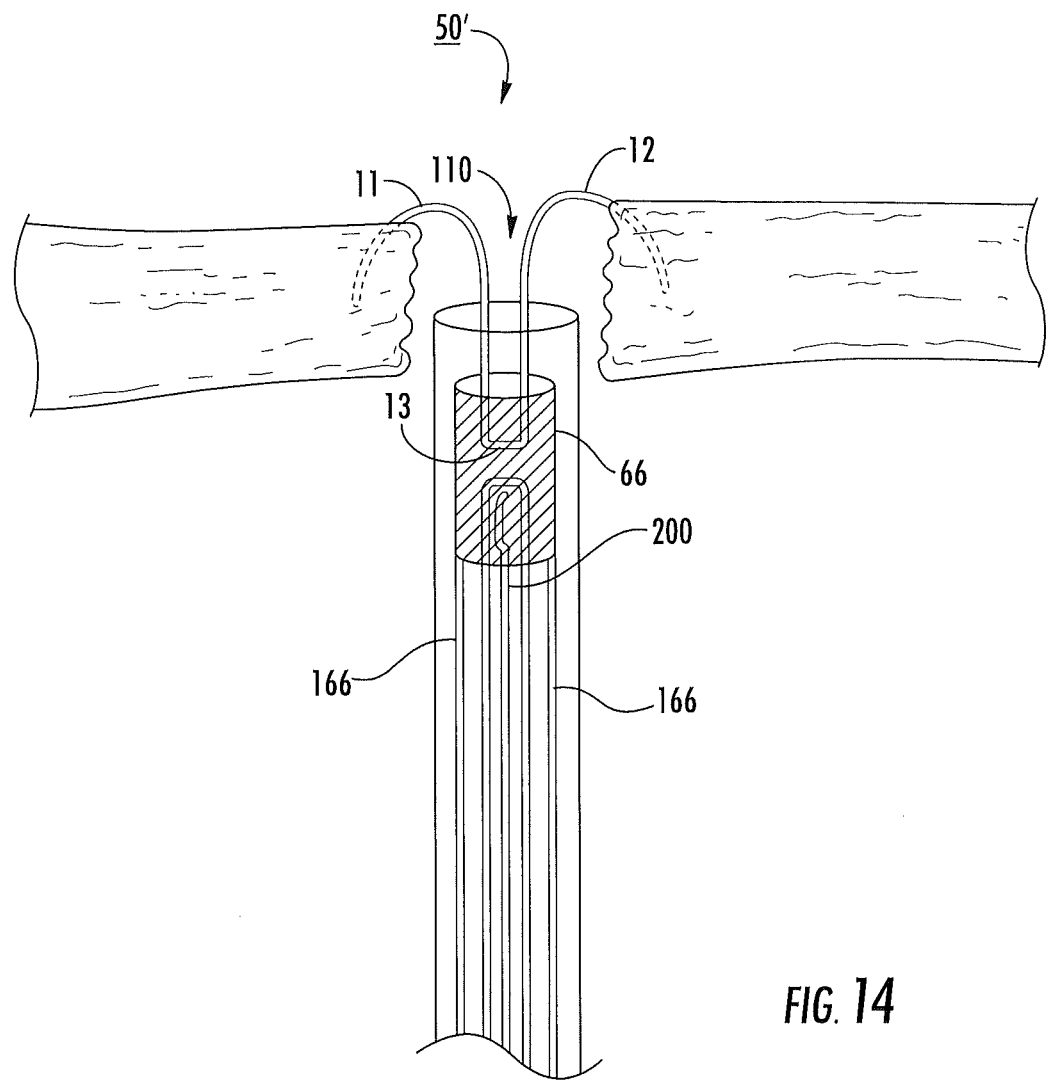
Figure 15:
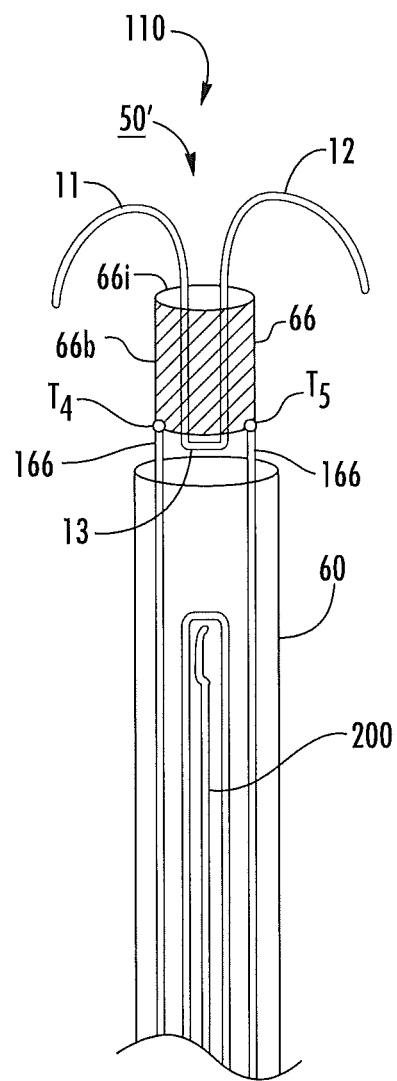
Figure 16:
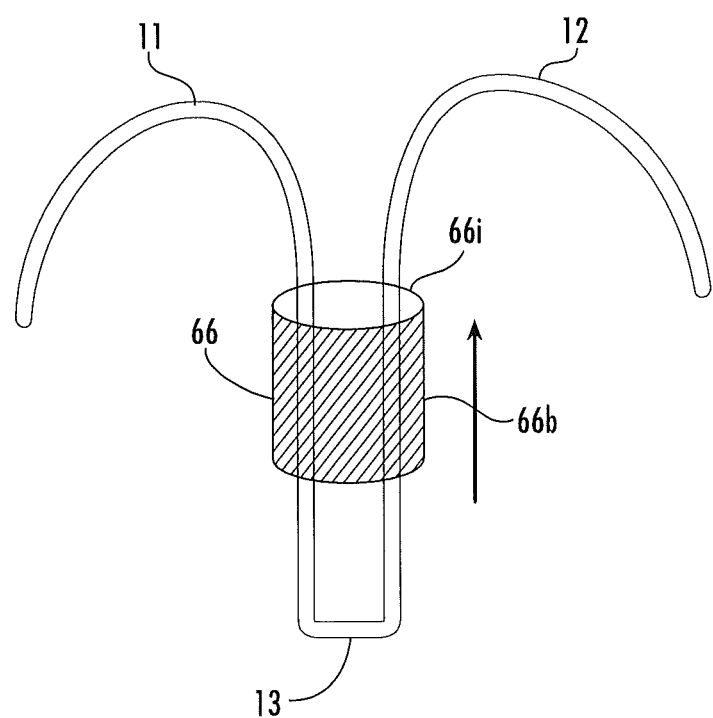
Figure 17:
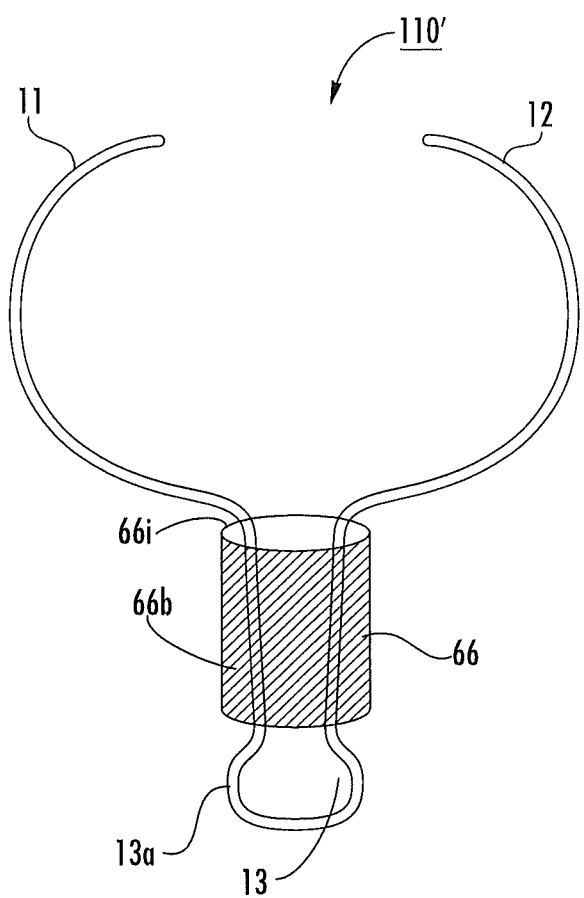
FIG. 17 is a schematic illustration of a closure device similar to that shown in FIG. 16, but with the prongs or legs opening outward instead of inward, e.g., away from the endoscope rather than toward the endoscope, according to embodiments of the present invention.

As shown in FIG. 13, as the shape memory structure 110 is pushed out it takes on the predefined shape with curvilinear (typically arcuate) shaped legs 11, 12 as discussed above connected by the crown 13. As shown in FIG. 14, once the member 110m is in target tissue e.g., anchored in or on serosa, the hook or other attachment member 201 holding the crown 13 in the device 50' is released. As shown in FIG. 15, the wires or other structures 166 holding the cinch 66 are pushed out of the sheath 60 so that the cinch 66 is snugly secured about a portion of the legs 11, 12 of the member 110m a distance inward of the crown 13. The legs 11, 12 can be pulled in through the cinch 66 as before the cinch is deployed. Alternatively, the cinch can be pushed forward over the legs before, during or after deployment. The wires or other structures 166 can then be released at anchor points T4, T5. FIG. 16 illustrates the closure device 110 deployed with the cinch firmly securing the legs 11, 12 of the structure 110m. Although not specifically shown, the prongs or legs can include more than two, such as the configurations shown with respect to FIGS. 8B-8D above, and may include barbs, spikes or other anti-slip features. FIG. 17 illustrates the device 110' can be configured to have the legs 11, 12 facing a different direction from that shown in FIG. 16 as discussed above with respect to the embodiments of FIGS. 9A-9C.

It is noted that although described as a single monolithic length of shape memory material configured to provide the member 110m in the embodiments discussed with respect to FIGS. 12-17, the device 110 can be formed as two separate members 110m that form the legs 11, 12 and the legs may be attached using another intermediate bridging member or separated but held in place via cinch 66.

Figure 18:
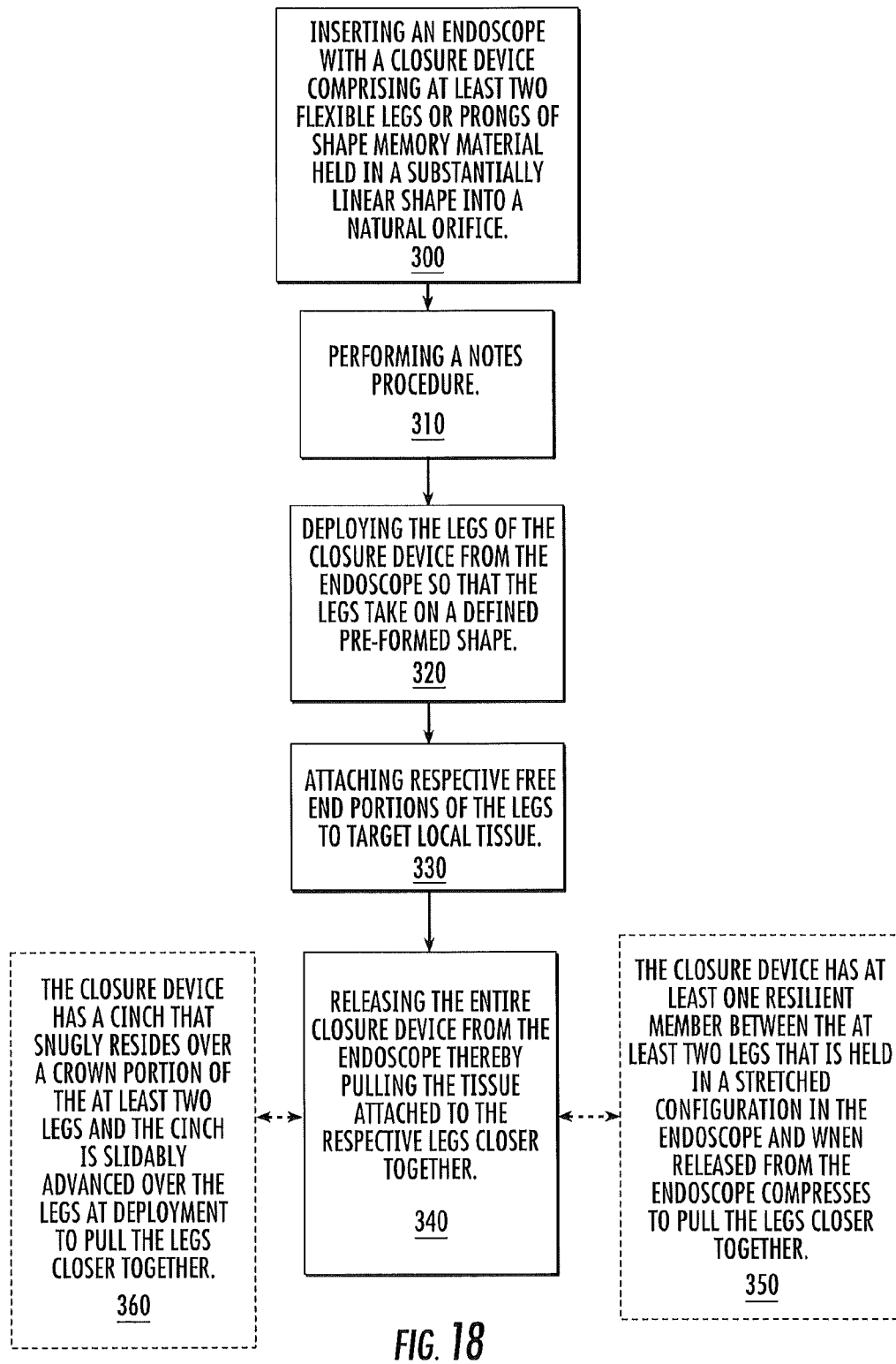
FIG. 18 is a flow chart of exemplary method steps that can be carried out according to embodiments of the present invention.

FIG. 18 is a flow chart of exemplary steps that can be used to carry out methods according to embodiments of the present invention. An endoscope with a closure device comprising at least two flexible legs or prongs of shape memory material held in a substantially linear shape can be inserted into a natural orifice (block 300). A NOTES procedure can be performed (block 310). The legs of the closure device can be deployed from the endoscope so that the legs take on a defined pre-formed shape (block 320). Respective free end portions of the legs can engage and/or attach to target local tissue (block 330). Then, the entire closure device can be released from the endoscope thereby pulling the tissue attached to the respective legs closer together (block 340).

In some embodiments, the closure device has at least one resilient member between the at least two legs that is held in a stretched configuration in the endoscope and when released from the endoscope compresses to pull the legs closer together (block 350). In other embodiments, the closure device has a cinch that snugly resides over a crown portion of the at least two legs and the cinch is slidably advanced over the legs at deployment to pull the legs closer together (block 360). Devices with both cinches and resilient bridging members may also be used.

While the closure devices and delivery tools are particularly suitable for endoscopic procedures and more particularly, NOTES procedures, the closure devices and/or delivery tools may also find use in other surgical procedures, including minimally invasive cardiac procedures.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A medical device, comprising:
    at least two spaced apart flexible legs comprising a shape memory material, each leg having a respective free end configured to engage local tissue; and
    at least one resilient member fixedly attached to each leg at a location away from the free end, wherein the resilient member is configured to take on a stretched configuration inside an endoscope during delivery while the legs reside closer together inside the endoscope, wherein the legs then expand to reside further apart when deployed from the endoscope.

2. The device of claim 1, wherein the at least one resilient member comprises an elastic band.

3. The device of claim 1, wherein the at least two spaced apart flexible legs are three spaced apart legs.

4. The device of claim 1, wherein the at least two spaced apart flexible legs are four spaced apart legs.

5. The device of claim 4, wherein the at least one resilient member is two, one attached to a first two of the legs and the other attached to a second two of the legs.

6. The device of claim 1, wherein the device is implantable in a patient, and wherein, implanted, the legs have a curvilinear shape and end portions away from the respective free ends are joined by the resilient member.

7. An endoscopic device delivery tool, comprising:
    an endoscope comprising a working lumen;
    a device sized and configured to be held in the lumen of the endoscope, the device having a resilient crown and at least two flexible elongate legs that terminate into tip ends comprising a shape memory material and having free end portions configured to attach to target tissue, wherein entire lengths of the legs including the tip ends are configured to have a straight configuration in the endoscope lumen, and wherein the legs take on a pre-formed curvilinear shape after deployment,
    a sheath configured to enclose the device and reside inside the endoscope lumen; and
    at least one elongate structure attached to the device and residing inside the sheath to be able to slidably deploy the device from the endoscope lumen, and wherein the at least one elongate structure comprises a tripod attachment structure that releasably holds the device at three spaced apart locations so that the resilient crown member is held in a "V" shape inside the sheath.

8. The device delivery tool of claim 7, wherein a distal end portion of the sheath is configured to slidably exit the endoscope lumen while holding at least a portion of the device therein.

9. The device delivery tool of claim 7, wherein the tool is configured to substantially concurrently release the tripod attachment structure after the legs of the device engage target tissue so that upon deployment from the sheath, the resilient member automatically pulls the legs closer together.

10. The device delivery tool of claim 7, wherein the device comprises a cinch that is configured to snugly hold a length of the legs of the device close together, wherein the cinch is slidably and entirely deployable out of the sheath.

11. The device delivery tool of claim 10, wherein the device comprises a continuous length of a shape memory material that is pre-shaped to have the two legs and the resilient crown, and wherein the at least one elongate structure includes a first one releasably attached to the cinch and a second one as the tripod attachment structure that is releasably attached to the crown to slidably advance the shape memory material legs out of the sheath before the cinch is released from the sheath.

12. The device delivery tool of claim 7, wherein the free end portions of the legs, outside the endoscope, face the endoscope and reside against or in tissue in a side of a hollow visceral wall opposing a side that the endoscope is located on.

13. The device delivery tool of claim 7, wherein the free end portions of the legs outside the endoscope face away from the endoscope.

* * * * *